United States Patent [19]
Manushakian

[11] Patent Number: 5,833,703
[45] Date of Patent: Nov. 10, 1998

[54] SURGICAL CUTTING TOOL

[75] Inventor: Hagop Samuel Manushakian, 67-73 Riding House Street, London W1P 7LD, United Kingdom

[73] Assignees: Hagop Samuel Manushakian; Martin Christopher Weisselberg, both of London, England

[21] Appl. No.: 737,551

[22] PCT Filed: May 12, 1995

[86] PCT No.: PCT/GB95/01088

§ 371 Date: Mar. 14, 1997

§ 102(e) Date: Mar. 14, 1997

[87] PCT Pub. No.: WO95/31144

PCT Pub. Date: Nov. 23, 1995

[30] Foreign Application Priority Data

May 13, 1994 [GB] United Kingdom .................... 9409625

[51] Int. Cl.⁶ ................................................. A61B 17/32
[52] U.S. Cl. ............................................. 606/174; 30/133
[58] Field of Search ................................. 606/170, 174, 606/205–210; 604/22; 30/133

[56] References Cited

U.S. PATENT DOCUMENTS

| | | |
|---|---|---|
| 2,751,908 | 6/1956 | Wallace . |
| 3,807,406 | 4/1974 | Rafferty et al. .......................... 606/174 |
| 4,049,002 | 9/1977 | Kletschka et al. . |
| 4,375,218 | 3/1983 | Digeronimo . |
| 5,071,418 | 12/1991 | Rosenbaum . |

FOREIGN PATENT DOCUMENTS

0 572 131  12/1933  European Pat. Off. .

*Primary Examiner*—William Lewis
*Attorney, Agent, or Firm*—McDermott, Will & Emery

[57] ABSTRACT

A surgical cutting tool, such as a pair of scissors, is provided suction means which allows suction to be applied to the site of operation. In the case of scissors, the closure of the blades is used to reduce the opening of a recess formed alone one of the inboard edges of the blades, and to effectively move the opening through which suction is applied, along the blade so as to constantly juxtapose the point of cutting. Electrodes can be connected to the blades to permit the tool to also act as a cautery.

16 Claims, 7 Drawing Sheets

SURGICAL CUTTING TOOL

This invention relates to a surgical cutting tool.

When using such a tool, for example surgical scissors, or a surgical scalpel, the surgeon normally needs to have at least one assistant who can carry out suctioning at the site where the surgical tool is being used, so as to remove blood and other body fluids which are released by the use of the tool and which would otherwise obscure the surgeon's field of view. Such an assistant may also carry out ancillary tasks, for example cauterization.

However, the need to involve an assistant has a number of disadvantages. One of these is that the carrying out of activities by the assistant at the same site as that where the surgeon is working may impede the surgeon's activities, and thus render them more difficult, or at least make the operation more lengthy. Furthermore, if it were not necessary for the assistant to carry suctioning and cauterization, the assistant might be more usefully employed in other tasks to assist the surgeon, and under some circumstances no assistant might be required at all.

According to the present invention there is provided a surgical cutting tool which is provided with means enabling suction to be applied to the site of operation of the tool. In two particularly preferred forms of the invention, the surgical tool is a pair of surgical scissors or a surgical scalpel. Optionally, the surgical tool may be provided with means for effecting cauterization.

The surgical cutting tool according to the invention may be provided with means for clamping tissue on which the surgeon is operating.

The invention will now be further described with reference to the accompanying drawings, in which.

Figures 1, 2, 3:
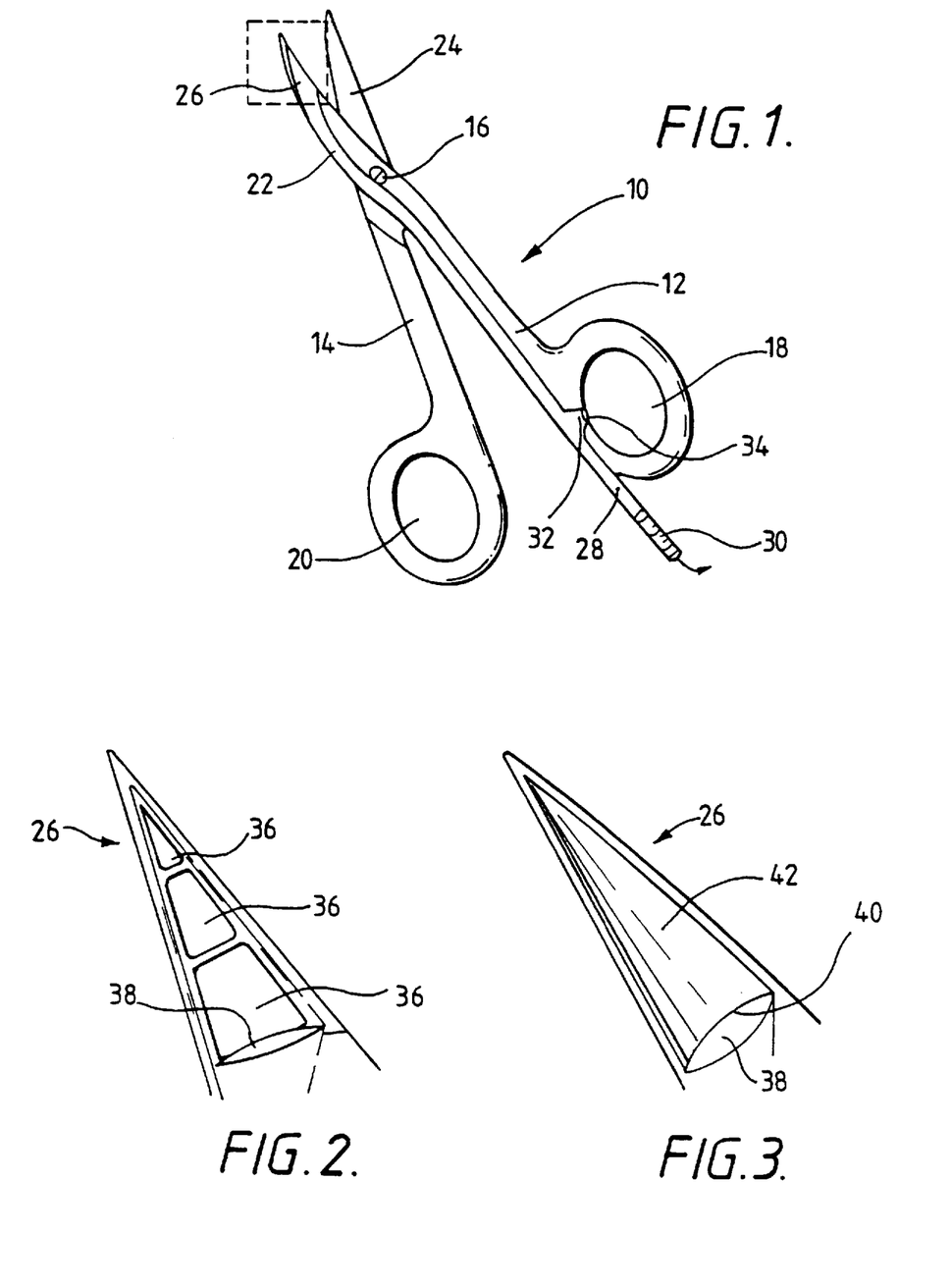
FIG. 1 shows a pair of surgical scissors according to the invention.
FIG. 2 shows a view on an enlarged scale of the tip of one type of blade which may be used in the scissors of FIG. 1.
FIG. 3 shows an alternative type of tip for use in the scissors of FIG. 1.

Referring to the embodiment of the invention shown in FIGS. 1 to 3, this is in the form of pair of surgical scissors 10 having members 12 and 14 which are connected by a pivot 16 and which have finger openings 18 and 20 respectively and blades 22 and 24 respectively.

The blade 24 can be conventional in construction, but the blade 22 has a tip portion 26 which is modified for the purposes of the present invention. One form of modified tip is shown on an enlarged scale in FIG. 2, and an alternative form of tip is shown on a similar scale in FIG. 3. The scissors are curved, as are the other embodiments of scissors described herein, and where any of the scissors are shown in plan view they are shown with the concave side facing the viewer. Alternatively, however, the invention, in its various aspects described herein, can be applied to scissors which are straight.

A suction tube 28, which is preferably of metal, though it could be of some other material, runs up-one edge of the member 12. The tube may be an entity distinct from the member 12 and merely attached thereto, but it is preferably a tube which is implanted in the member 12. Such implantation could be achieved, for example, by forming a bore in the member 12 and inserting the tube lengthwise in it, or forming a recess in the back edge of the member 12 and inserting the tube into that. In the latter case the exposed portion of the tube might be covered, for example by solder material. A further possibility would be not to have a separate tube 28 as such and rely on a bore in the member 12 to achieve the same effect. For simplicity of description, such a bore is regarded in the ensuing description as itself constituting a tube.

One end of the tube is attached to a flexible tube 3D which in turn is connected to a source of suction (not shown). The other end of the tube terminates in the tip 26, as is described below. The tube 28 hag a short branch 32 which communicates with atmosphere via an orifice 34 located in the finger opening 18. The orifice 34 allows a small amount of air to enter the tube 28, and thus, when it is open, reduces the suction effect applied at the tip 26. The surgeon can thus control the amount of applied suction by closing the orifice 34, or opening it wholly or partially, using that one of his fingers which is in the finger hole 18 (this being, under normal circumstances, the surgeon's thumb).

In the embodiment of tip shown in FIG. 2, at least one aperture 36 (three such apertures are shown, though there could be a greater or lesser number) extends through the blade from one face to the other. The upstream end 38 of the suction tube 28 is positioned adjacent one edge of the largest of the three apertures. The tip shown in FIG. 2 provides a significant suction effect only when the scissors are at least partially closed, and control of the suction effect can therefore be achieved by opening and closing the scissors. Additional control, when the scissors are at least partially opened, can be achieved by opening and closing the orifice 34.

In the embodiment of tip shown in FIG. 3, a part-conical depression is formed in that surface of the tip which faces towards the viewer as seen in FIGS. 1 and 3, i.e. the surface which faces away from the blade 24. Suction is here controlled solely by means of the orifice 34.

Figures 4, 5A, 5B, 5C, 5D:
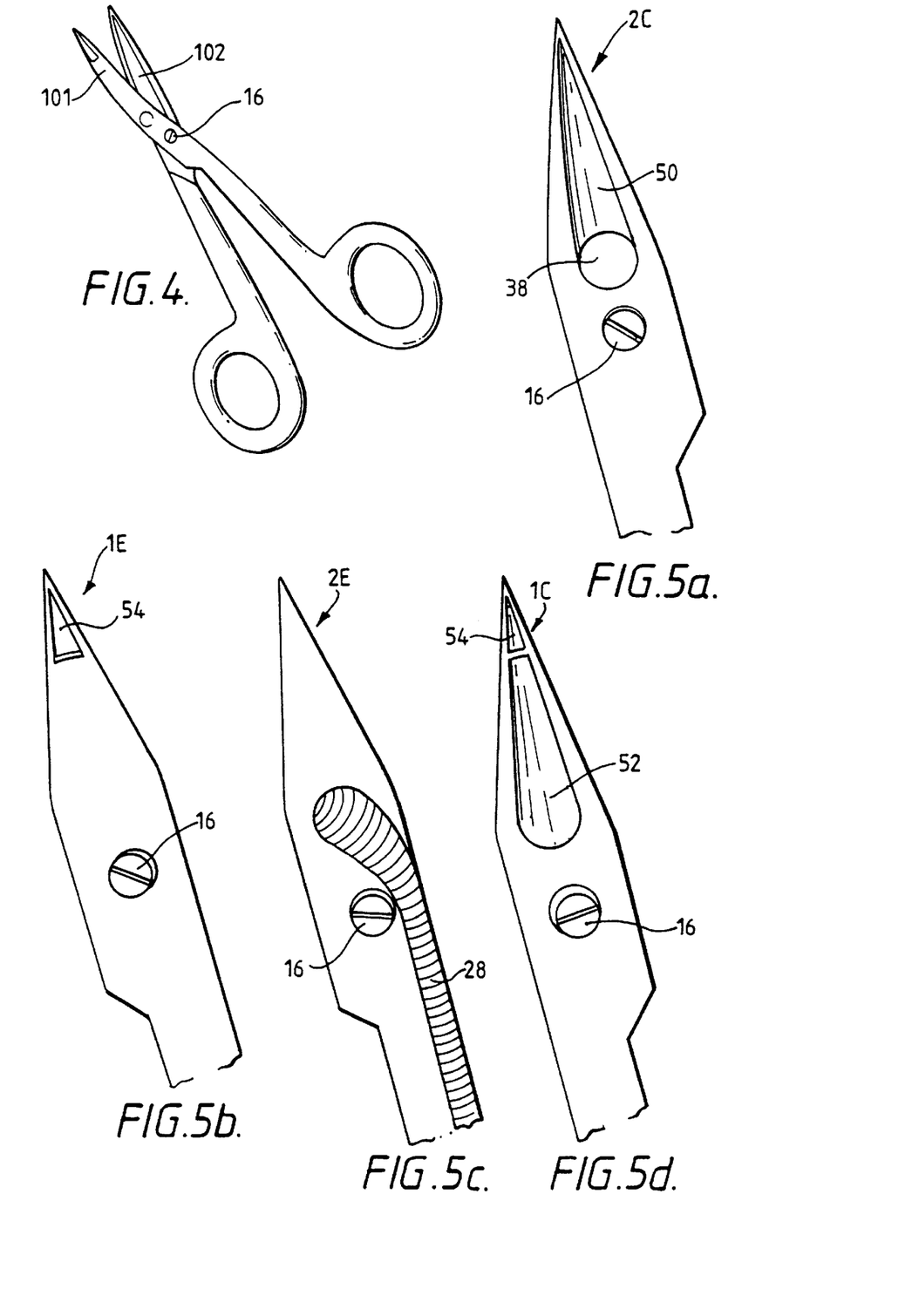
FIG. 4 shows a second embodiment of surgical scissors according to the invention.
FIGS. 5*a* to 5*d* show a first combination of scissor tip configurations which can be used in the scissors of FIG. 4.
Figures 6A, 6C:
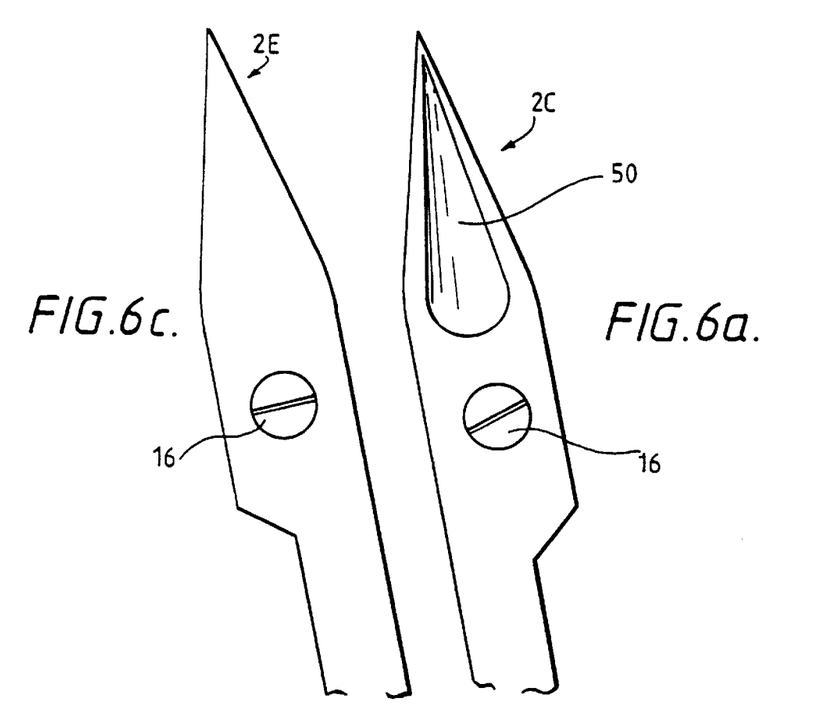
FIGS. 6*a* to 6*d* show a second combination of tip configurations which can be used in the scissors of FIG. 4.
Figure 6B:
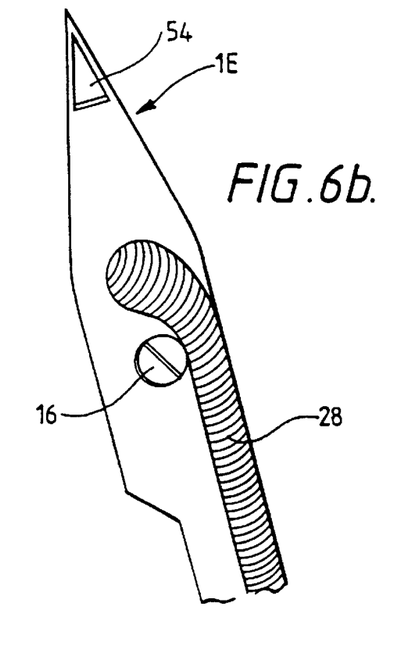
Figure 6D:
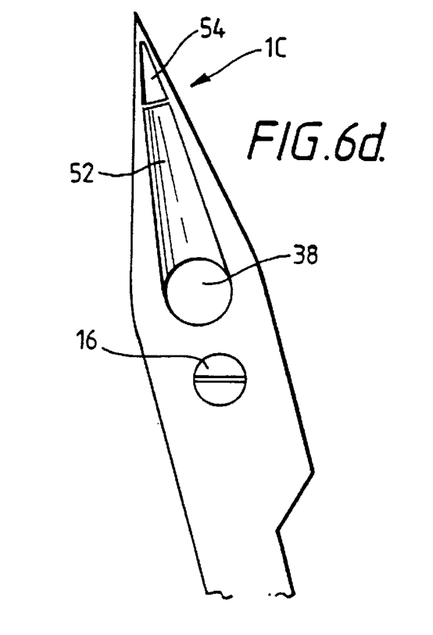

Two further embodiments of the invention will now be described with reference to FIGS. 4, 5 and 6. In FIG. 4, a pair of surgical scissors is denoted as having a blade 101 and a blade 102, with the cutting surfaces of the blades being denoted below using a suffix C (1C is the cutting surface of blade 101 and 2C is the cutting surface of blade 102), and exterior surfaces of the blades (i.e those which face away from one another) being denoted by the suffix E (with 1E denoting the exterior surface of blade 101 and 2E denoting the exterior surface of blade 102).

FIGS. 5a to 5d show one possible combination of these four surfaces. Surface 2C shown in FIG. 5a has a part-conical recess 50, the larger end of which communicates with the upstream end 38 of the suction tube 28. From this it will be understood that in this embodiment the suction tube is provided in the blade 102. This can be seen more clearly in FIG. 5c, which shows surface 2E. The surface 10 of blade 101 has a part-conical recess 52 which matches the recess 50 in surface 2C, except at the distal end, where a triangular aperture 54 extends through the blade and is thus visible also on surface 1E (see FIG. 5b). Suction is applied by the scissors to the operating site via the aperture 54 when the scissors are at least substantially closed. When they are open it is applied via the grooves 50 and 52.

FIG. 6a to 6d show an alternative set of surfaces which can be used. In this embodiment, the suction tube 28 is provided on blade 101, with its upstream end 38 opening into surface 1C shown in FIG. 6d. This has the consequence that surface 2E is a regular blade surface, without any additional features resulting from the application of the present invention.

FIGS. 7a to 7d show how a pair of surgical scissors may be provided with means for clamping the patient's tissue. For simplicity, FIGS. 7a to 7d do not show any means for providing the scissors with suction. It is to be understood, however, that such suction means could be provided in the structure shown in FIGS. 7a to 7d, though suction means need not provided.

Figure 7A:
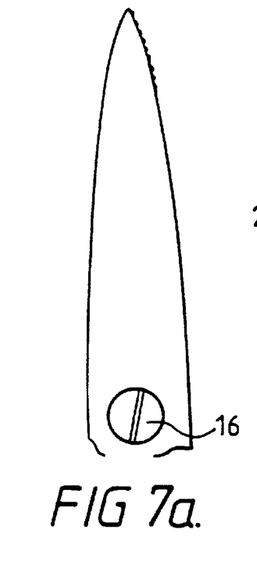
FIGS. 7*a* to 7*d* show the incorporation of a clamp in a pair of surgical scissors, and are respectively a plan view with the scissors closed, a plan view with the scissors open, a side view with the scissors closed, and a side view with the blades separated for the sake of clarity, to show their construction.
Figure 7B:
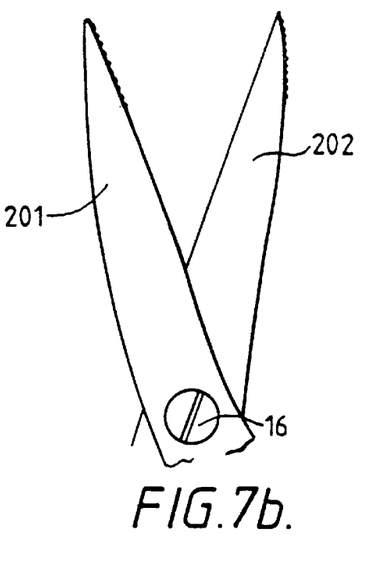
Figure 7C:
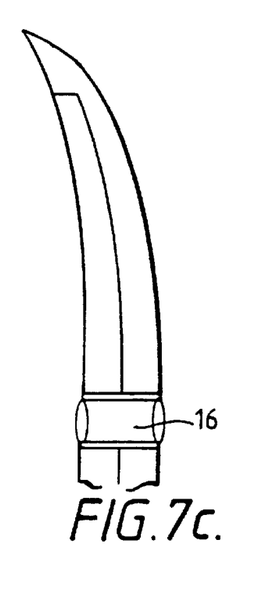
Figure 7D:
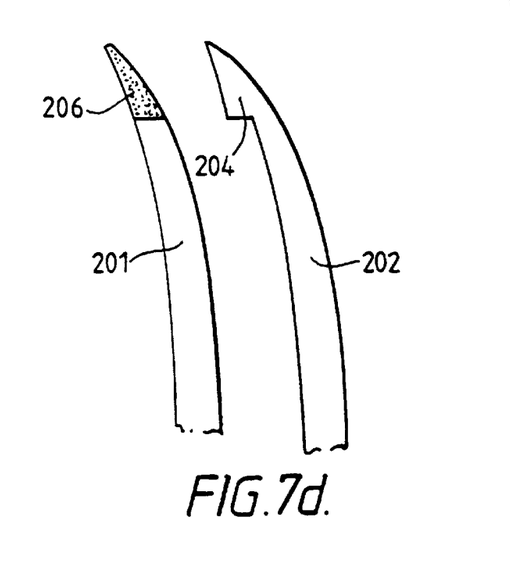

The scissors of FIGS. 7a to 7d are shown as having a pair of blades 201 and 202, with the tip of blade 202 having a clamp member 204 which, as considered in the view of FIGS. 7c and 7d, overlaps the tip of the blade 201. The blade 201 has, at its tip, a portion which is cut away to define a recess with which the clamp portion 204 can mate, so that when the scissors are closed the face 206 which is thus formed on the blade 201, and which is visible in FIG. 7d, bears against that face of clamp portion 204 which, as viewed in FIG. 7d, is remote from the viewer.

Figure 8:
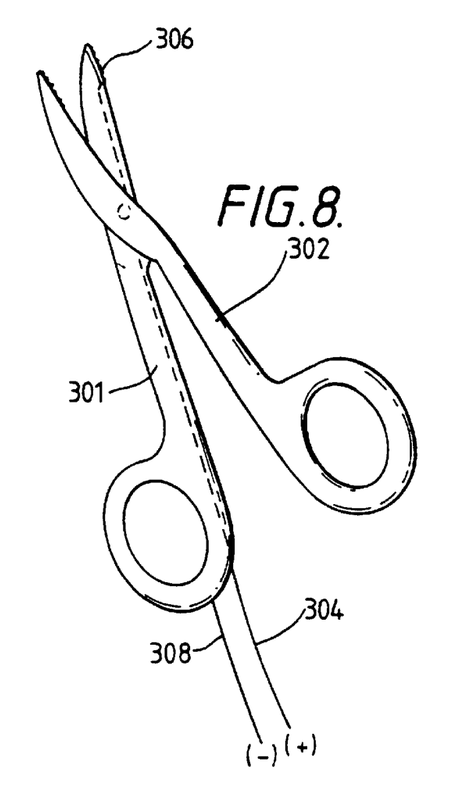
FIG. 8 shows a pair of scissors incorporating means for cauterization.

FIG. 8 shows the provision of a pair of surgical scissors with a cautery for effecting cauterization. One terminal (it is illustrated as being the positive terminal, but it could alternatively be the negative terminal) of an electrical supply is connected to a wire 304 which runs along one of the members 301 constituting the scissors (the other of the members is denoted by reference numeral 302) and terminates in a tip portion 306 which is electrically isolated from the remainder of the member 301. It will be understood that the wire 304 is insulated from the member 301 except where it is in electrical contact with the tip 306. The other wire 308 is electrically connected directly to the member 301, and indirectly to the member 302 through the pivot 16. A bipolar cautery is thus formed. It a unipolar cautery were desired, one of the wires 304 and 308 would be omitted, and the other connection would be made to the patient's body. For ease of illustration FIG. 8 does not show any means for providing suction to the scissors. It is to be understood, however, that such suction means might be provided, though they need not be. It is also to be understood that the cautery arrangement of FIG. 8 could be combined with the clamp arrangement of FIGS. 7a to 7d, with or without a suction arrangement.

Figure 9:
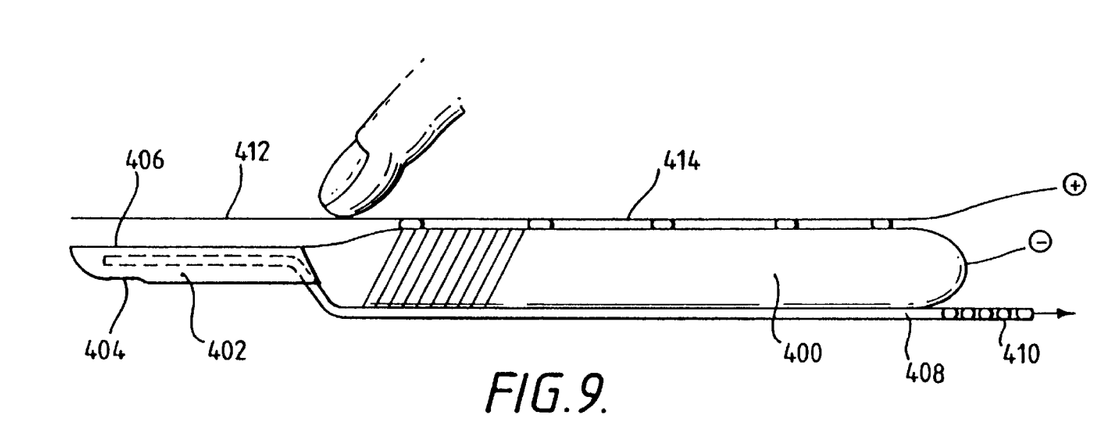
FIG. 9 is a side view of a scalpel according to the present invention, incorporating both suction and cauterization means.
Figures 10, 11:
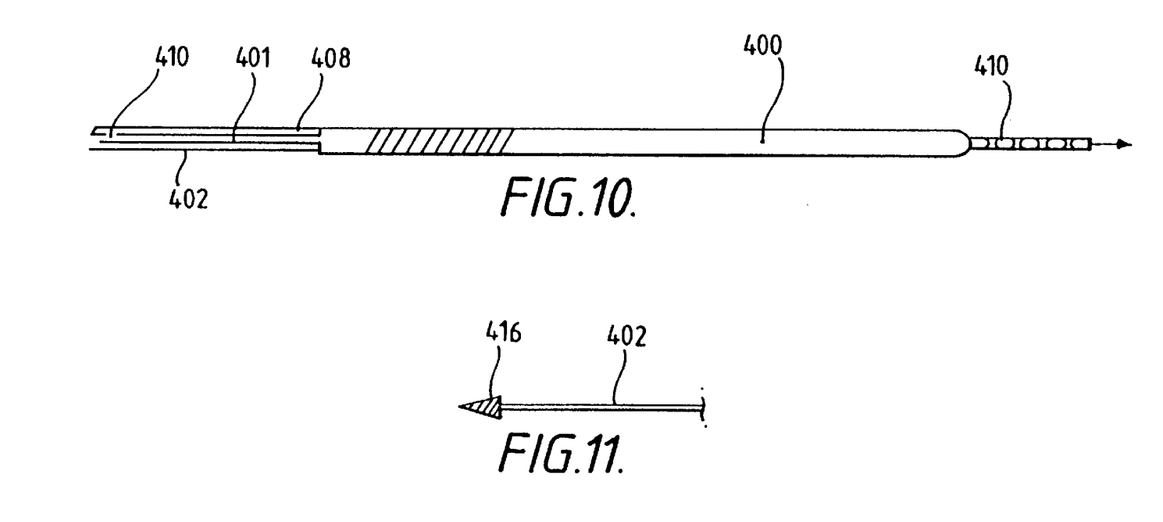
FIG. 10 is a view taken at right angles to FIG. 9, from the dorsal aspect or the scalpel showing the same scalpel, but with a forceps tip and metallic extension thereof omitted for clarity.
FIG. 11 illustrates a modified scalpel blade, seen from the non-cutting edge thereof.

FIGS. 9 and 10 illustrate an embodiment of the invention in the form of a scalpel. This is provided both with means for providing suction, with clamping means, and with a cautery. The scalpel comprises a handle 400 having blade holder 401 which carries a blade 402. The blade has a cutting edge 404 and non-cutting edge 406. A suction tube 408 runs along the lower edge of the handle, and thence along one face of the blade 402, to terminate in a suction tip 410. The suction tip faces towards the adjacent face of the blade 402, as can be seen in FIG. 10. The downstream end of the tube 408 is connected to a flexible tube 410 which, in turn, is connected to a source of suction (not shown).

A forceps tip 412 is positioned above, but normally spaced from, the non-cutting edge 406 of the blade 402. The forceps tip 412 is electrically isolated from the handle 400, on which it is mounted. The forceps tip is made of a flexible material, for example spring steel, and can thus be pressed resiliently towards the edge 406, to clamp tissue, for example a piece of tissue which is bleeding, between the forceps tip and the edge 406. The forceps tip 412 is connected via a metallic extension 414 (which is electrically isolated from the handle 400) to one pole of an electrical supply (here shown as the positive pole). The handle 400, and hence the blade 402, is connected to the other pole, here shown as the negative pole. Accordingly, when bleeding tissue is clamped, as described above, it is subjected to a cauterizing action by the electrical current which passes through it, being clamped while cauterization is taking place.

FIGS. 9 and 10 illustrate a bipolar cautery, but a unipolar cautery could be produced by omitting one or other of the electrical connections, and making that connection to the patient's body.

FIG. 11 illustrates a modified scalpel blade, in which the tip thereof has a triangular piece 416 formed thereon. The piece 416 can be a separate item which is secured to the blade by suitable means, or it can be formed integrally therewith in the course of manufacture of the blade. The forceps tip preferably has a triangular piece formed at its distal end which is identical in shape and size to the triangular piece 416 formed on the blade.

Figure 12:
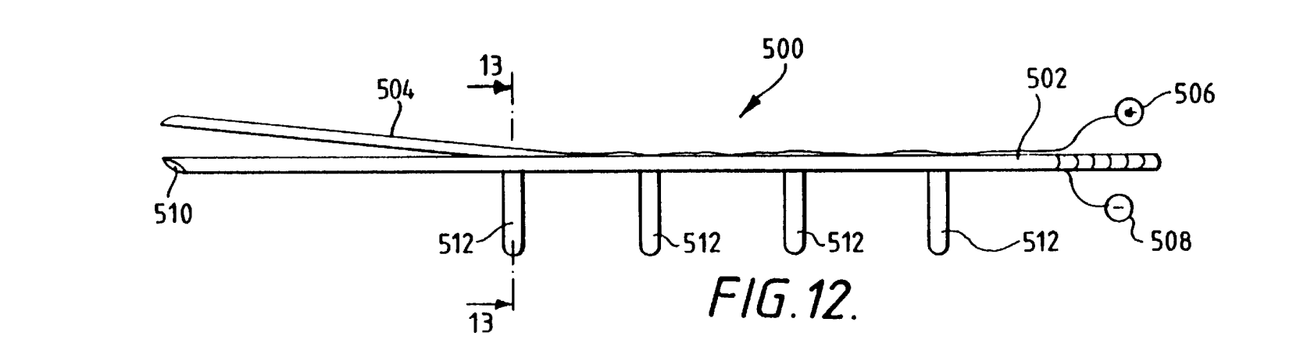
FIG. 12 is a side view of a suction/cautery unit provided with means for removably receiving a scalpel.
Figure 13:
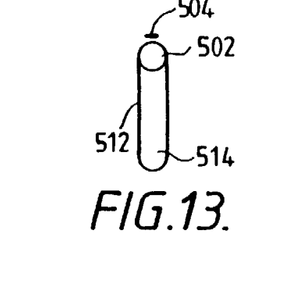
FIG. 13 is a section taken on line 13—13 in FIG. 12.

FIGS. 12 and 13 show a combined suction/cautery unit 500. This comprises a suction tube 502 made, for examples, from metal or a plastics material, to which is secured a forceps member 504 made of metal. The forceps member 504 is resiliently flexible and can be urged towards the tube 502. One terminal 506 of an electrical power supply is electrically connected to the forceps member 504. The other pole is connected to the suction tube 502 if the latter is of conductive material (in which case the tube and forceps member must be electrically isolated from one another) or, if the tube is not of conductive material, a conductive wire extends through the tube from the pole, to emerge at the tube exit 510. The other end of the tube 502 is connected to a suction source (not shown).

A plurality of U-shaped guides 512 extend from the tube 502 in a direction away from the forceps member 504. The guides are aligned with one another, and define aligned openings 514 in which a surgical scalpel (not shown) can be received, preferably so as to be removable. In this way the surgeon has the option of using the scalpel alone, or combined with the suction and/or cautery unit, depending on the particular operation. Alternatively, the suction/cautery unit can be used without the scalpel. The suction/cautery unit is sufficiently simple that it should be economical for it to be manufactured, if desired, as a disposable item.

The embodiment of FIGS. 14 to 17 is in the form of forceps 600 comprising first and second forceps arms 601 and 602 which are movable resiliently towards one another. The second forceps arm 602 has a recessed area 603 in which is mounted a blade holder 604. This is of a shape to be received in a slot 605 of a surgical blade 606.

Figure 14:
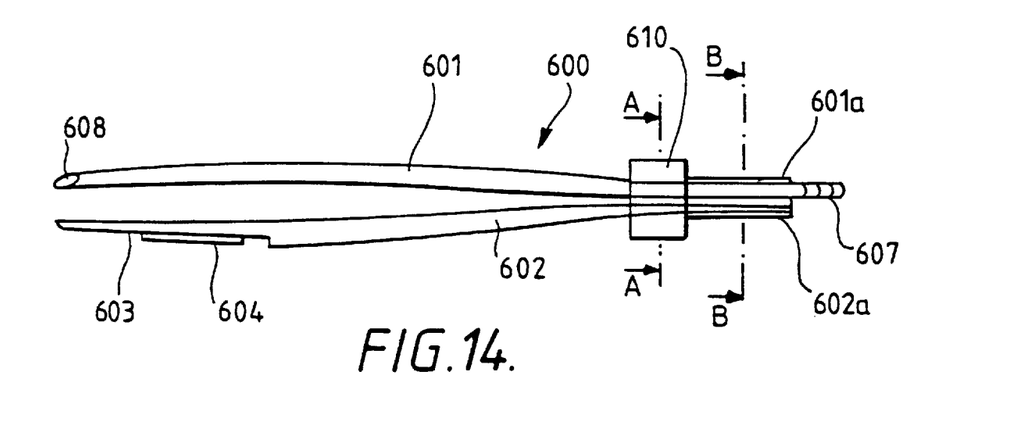
FIG. 14 shows a further embodiment in the form of a pair of forceps provided with a blade holder.
Figure 14A:
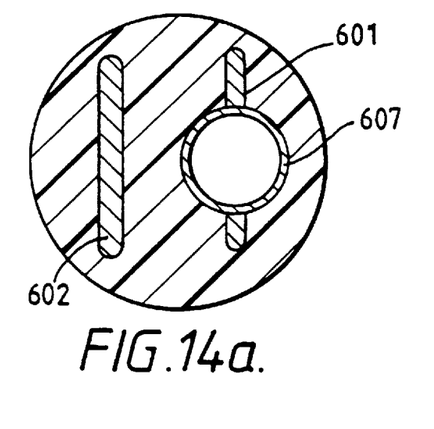
FIGS. 14*a* and 14*b* are cross sections through the forceps of FIG. 14, on a larger scale, taken on lines A—A and B—B respectively.
Figure 14B:
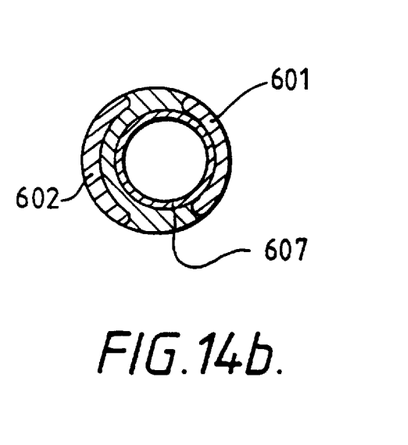
Figure 15:
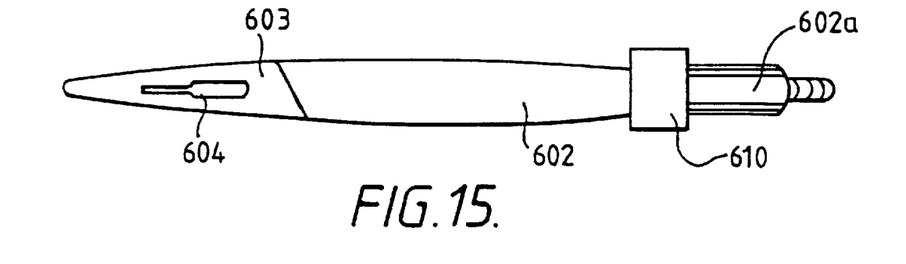
FIG. 15 shows the forceps or FIG. 14 in a view taken at right angles thereto.
Figure 16:
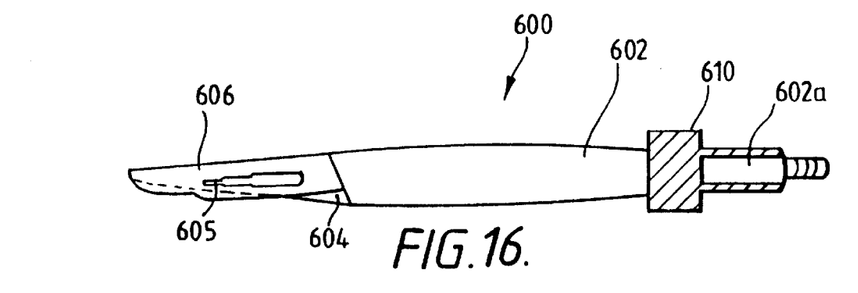
FIG. 16 shows the forceps in the view of FIG. 15, but with a blade in position.
Figure 17:
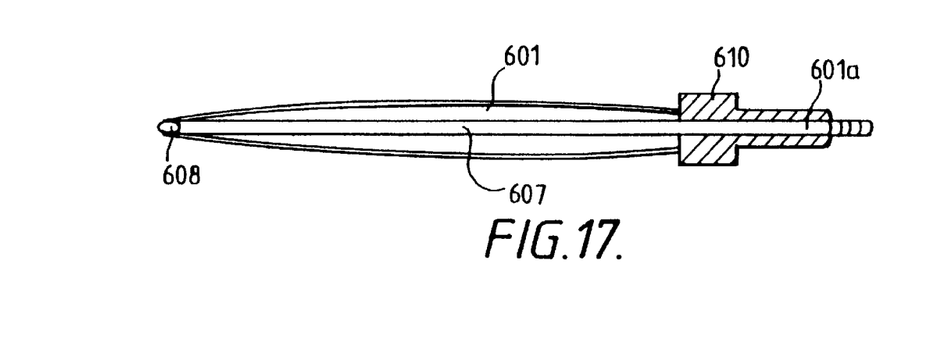
FIG. 17 shows the forceps in a view at 180° to that of FIG. 15.

The forceps arm 601 is provided with a suction tube 607 formed or implanted therein, which can be connected at the proximal end to a source of reduced pressure and which terminates at the distal end in an open tip 608.

The proximal end of the forceps carries an arm housing 610 made of plastics or other insulating material. (The housing 610 is drawn as though it were transparent, so that the structures within it are visible). The forceps arms 601 and 602 are held therein in fixed position and in electrical isolation from one another. Portions 601a and 602a are exposed for electrical connection to respective poles of a bipolar electrical power supply which enables the distal tips of the forceps members to act as a cautery. Alternatively, only one of the forceps arms would have an electrical connection made to it, for use in unipolar cauterisation.

The embodiment of FIGS. 14 to 17 can thus be used as a pair of forceps and as a cutting tool, to which both suction and cauterisation can be applied. If in any particular situation it is desired not to use its cutting function the blade 606 can simply be omitted.

It should be noted that various of the features described above may be used without a means for applying suction being provided. For example, the surgical cutting tool may be provided with the clamping and/or cauterisation features without suction, and a combined forceps/scalpel unit may be provided without suction. Also, the suction and clamping features may be combined in a tool which is not a cutting tool, i.e. as in FIGS. 12 and 13, but without the scalpel guide means.

I claim:

1. A pair of surgical scissors comprising:

first and second blades each having a cutting surface and an exterior surface, the cutting surfaces facing one another;

suction means for enabling suction to be applied to the site of operation of the scissors, wherein said suction means comprises a suction passage which terminates in a suction opening which opens into the cutting surface of one of the blades, the cutting surfaces being so formed as to define between them, as they close, a channel for communicating suction distally of the suction opening.

2. A pair of scissors according to claim 1, wherein the pair of scissors comprises a pair of finger grips and the passage has a control opening which opens to atmosphere in the region of one of the finger grips to be at least partially closable by a finger of a user.

3. A pair of scissors according to claim 1, wherein the channel communicates, via at least one aperture extending through one or both blades, with the exterior surface of one or both blades.

4. A pair of scissors claim 3, wherein there is a plurality of the apertures spaced longitudinally from one another.

5. A pair of scissor as claimed in claim 1, wherein the channel is defined in part by a depression formed in the cutting surface of at least one of the blades.

6. A pair of scissors according to claim 1, wherein one of the blades has a protrusion at its distal end which extends toward the other blade, and wherein the other blade has a recess adapted to receive the protrusion when the scissors are closed and to enable material to be clamped between the protrusion and the recess.

7. A pair of scissors according to claim 1, comprising means for making at least one electrical connection with the scissors to enable them to act as a cautery.

8. A pair of scissors according to claim 7, comprising a first electrical conductor electrically connected to the distal end of one of the blades, and a second electrical conductor electrically connected elsewhere to the scissors.

9. A pair of surgical scissors comprising:

first and second blades which respectively have first and second cutting surfaces which face one another, and suction means for enabling suction to be applied to the site of operation of the tool, said suction means comprising:

a suction passage which terminates in a suction opening, and an elongate recess which communicates the suction opening with the suction passage and which is formed in the first cutting surface so as to extend continuously therealong and which is so arranged that as the scissors close, the amount of the elongate recess which is left open by the second cutting surface, is continuously reduced and so that a line of suction established effectively moves toward a tip of the first blade in which the recess is formed.

10. A pair of scissors according to claim 9, wherein the elongate recess is partitioned into a plurality of segments in a manner wherein each of the segments being in constant fluid communication with the suction passage.

11. A pair of scissors according to claim 9, wherein the first and second blades have first and second finger grips respectively, and wherein the suction passage has a control opening which opens to atmosphere in the region of one of the first and second finger grips so as to be at least partially closable by a finger of a user.

12. A pair of scissors according to claim 9, wherein the suction opening communicates, via at least one aperture extending through one or both blades, with an exterior surface of one or both of the first and second blades.

13. A pair of scissors according to claim 12, wherein there is a plurality of the apertures spaced longitudinally from one another.

14. A pair of scissors according to claim 9, wherein the first blade has a protrusion at its distal end which extends toward the second blade, and wherein the second blade has a recess adapted to receive the protrusion when the scissors are closed, to enable material to be clamped between the protrusion and the recess.

15. A pair of scissors according to claim 9, comprising means for making at least one electrical connection to the scissors and for enabling them to act as a cautery.

16. A pair of scissors according to claim 15, comprising a first electrical conductor electrically connected to one of the first and second blades, and a second electrical conductor electrically connected elsewhere to the scissors.

* * * * *